United States Patent [19]

Heller et al.

[11] Patent Number: 4,818,096
[45] Date of Patent: Apr. 4, 1989

[54] PHOTOREACTIVE LENSES WITH ADAMANTANE SPIRO COMPOUNDS

[75] Inventors: Harry G. Heller, Cardiff, Wales; Stephen N. Oliver, Felixstowe, England; John Whittall, Caerphilly, Wales; Jack Brettle, Towcester, England; Clive Trundle, Towcester, England; Martin W. Baskerville, Towcester, England

[73] Assignee: The Plessey Company plc, Ilford, England

[21] Appl. No.: 63,054

[22] Filed: Jun. 17, 1987

[30] Foreign Application Priority Data

Jun. 17, 1986 [GB] United Kingdom ............... 8614680

[51] Int. Cl.$^4$ .................. G02B 27/00; C07D 265/00; G03C 1/733
[52] U.S. Cl. .................................. 351/163; 350/354; 252/586
[58] Field of Search ............... 544/70; 351/163, 161; 350/354; 548/407; 549/24, 26, 42, 43, 44, 48, 264, 331, 345; 252/586

[56] References Cited

U.S. PATENT DOCUMENTS

| | | | |
|---|---|---|---|
| 2,542,386 | 2/1951 | Beattie | 18/58 |
| 3,231,584 | 1/1966 | Berman | 260/319 |
| 3,404,861 | 2/1966 | Ewer | 249/187 |
| 3,567,605 | 3/1971 | Becker | 204/158 |
| 3,627,690 | 12/1971 | Casella et al. | 252/586 |
| 3,944,637 | 3/1976 | Bond et al. | 264/1 |

FOREIGN PATENT DOCUMENTS 0246114 11/1987 European Pat. Off. .
2146327 4/1985 United Kingdom .

OTHER PUBLICATIONS

J. Org. Chem., vol. 40, No. 8, 1975, pp. 1142–1149, Albert Padwa, "Photochemical Ring-Opening Reactions of Substituted Chromenes and Isochromenes".

Primary Examiner—Matthew A. Thexton
Assistant Examiner—Catherine S. Kilby
Attorney, Agent, or Firm—Sughrue, Mion, Zinn, Macpeak, and Seas

[57] ABSTRACT

Photoreactive plastics lenses are disclosed which are coated or impregnated with an adamantane 2-spirobenzo or naphthopyran and with a blue coloring photochromic benzo- or naphthopyran having a nitrogen containing substituent in the 2-position in the pyran ring. The lenses darken in sunlight and fade rapidly at ambient temperatures in the dark or in white light which does not contain a U.V. component. The combination of the yellow/orange coloring adamantane 2-spiro pyran compound with the purple/blue coloring pyran gives a desired brown/grey coloration in the sunlight-darkened lens. The invention includes novel blue-coloring pyran compounds in which the nitrogen-containing substituent in the 2-position is a phenyl group having an amino or substituted amino or nitrogen-containing heterocyclic substituent in the ortho- or para-position of the phenyl group.

The basic chromene structure and the suffix N will be used to distinguish the blue-coloring pyran compounds having a nitrogen-containing substituent, namely:

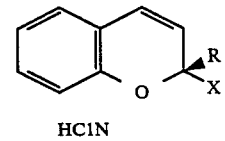

HC1N

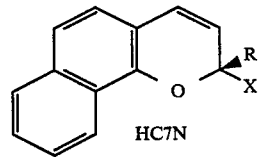

HC7N

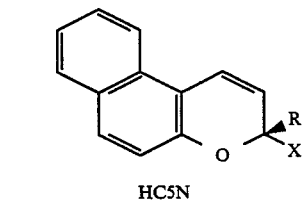

HC5N

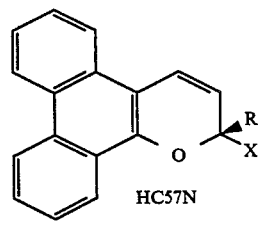

HC57N

12 Claims, 11 Drawing Sheets

PHOTOREACTIVE LENSES WITH ADAMANTANE SPIRO COMPOUNDS

BACKGROUND OF THE INVENTION

This invention relates to photoreactive lenses and to photochromic compounds and compositions for rendering lenses photoreactive.

DESCRIPTION OF THE PRIOR ART

Conventional commercial photoreactive lenses, i.e. lenses which darken in sunlight and lighten again in the shade, are manufactured from glass and utilise the reversible formation of silver particles from dispersed silver halide salts to bring about the darkening of the lenses.

Plastic lenses have advantages over glass; principally they are lighter in weight (particularly in the case of opthalmic lenses having high powers) and less prone to breakage. Since the above described action of dispersed silver salts does not take place in plastics matrices, attempts have been made to develop photochromic compounds which would produce the same kind of effect in plastics materials. The ideal compound for this purpose should, when absorbed or coated on a conventional plastics lens, possess the following properties i.e.

(a) a high quantum yield for colouring in the near ultra-violet (b) a low quantum yield for bleaching with visible light (c) a fast thermal fade at ambient temperatures.

Unfortunately, these properties are also generally associated with thermal or photochemical instability so that the useful life of sunglasses incorporating such compounds would be too short for commercial feasibility.

U.S. Pat. No. 3,567,605 (Becker) describes a series of pyran derivatives, including certain benzopyrans and naphthopyrans, but not spiro-compounds, which exhibit photochromic properties. These compounds can be regarded as derivatives of chromene. Typically, the compounds undergo a colourless to yellow-orange change on irradiation by U.V. light. However, the observation of this behaviour by Becker was restricted to temperatures below about −40° C. and Becker reported that the colour change was reversed when the temperature was raised to a temperature in the range of −10° C. to 0° C.

Padwa et al in J. Org. Chem., vol. 40, No. 8, 1975, page 1142, examined the photochemical reactions of compounds of the kind described by Becker, identified the by-products and suggested pathways to ring-opened coloured intermediates and the final non-coloured phenolics. The coloured forms examined by Padwa were unstable at room temperature, at which temperature he suggested that the coloured quinoneallide intermediates either thermally revert to the starting material or undergo 1,4 addition of the methanol solvent to form the corresponding phenolic ether product or a 1,5-hydrogen shift in acetone to form the corresponding phenol. However, Padwa does not suggest ways in which the stability of the compounds he examined might be improved nor any modification which might be made to the structure of known pyran compounds in order to induce photoreactive behaviour in a plastics lens.

The required properties of a photochromic compound for sunglasses application are outlined above and compounds which possess these properties have been termed "heliochromic" compounds in U.K. Pat. No. 2146327. Thus, the term "heliochromic" compound is used in this specification to mean a compound which possesses the following properties, namely (a) a high quantum efficiency for colouring in the near ultra-violet, (b) a low quantum yield for bleaching with visible white light and (c) a fast thermal fade at ambient temperature but not so rapid that the combination of white light bleaching and thermal fade prevent colouring by the U.V. component of strong sunlight. Such properties make the compound eminently suitable for use in photoreactive lenses.

In our U.K. patent application No. 8611837, now application No. 050,101, there is described a series of photochromic adamantane spiropyrans which possess the above-described desirable heliochromic properties, in conjunction with good thermal and photo-chemical stability. These adamantane spiropyrans can also be incorporated into standard plastics lens materials, such as CR39 by imbibition and members of this series have been shown to be capable of undergoing a large number of cycles without significant degradation.

It is thought that the reason why the compounds in our above application exhibit these improved properties is that in accordance with Bredt's rule, the spiro-carbon cannot become doubly-bonded and therefore the ring-opened coloured form is resistant to degradations associated with 1,5-hydrogen shift.

However, one limitation of the compounds of this series is that the compounds which show the best resistance towards degradation exhibit a colour change on exposure to a U.V. light (or sunlight) from colourless to yellow/orange. The market demand is, however, largely for lenses which darken to brown or grey. Although as indicated in our above copending patent application a photoreactive lens can be produced by incorporating into the lens a blend of a yellow and a blue photochromic compound, in practice, it has proved difficult to prepare purple/blue colouring photochromic compounds whose resistance to degradation or fatigue is equivalent to that of the best of the yellow colouring adamantane spiropyrans.

SUMMARY OF THE INVENTION

According to one aspect of the present invention there is provided an opthalmic or planoplastics lens which darkens in sunlight and reverts to a pale or colourless condition in white light at normal ambient temperatures, wherein the lens has incorporated therein or coated thereon at least two heliochromic compounds, one of said compounds comprising a spirobenzopyran or spironaphthopyran in which an adamantane group is present in the 2-spiro-position of the benzopyran or naphthopyran ring and a second compound comprising a benzo or naphtho-pyran having a nitrogen-containing substituent in the 2-position of the pyran ring. The blue colouring pyran compounds of the invention are based on the same basic chromene structures as the adamantylidene spiropyrans described in our above copending applifation. For ease of description the same code will be employed as in our co-pending application to designate the basic chromene structure and the suffix N will be used to distinguish the blue-colouring pyran compounds having a nitrogen-containing substituent, viz:

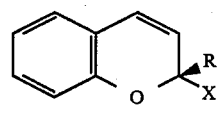

HC1N

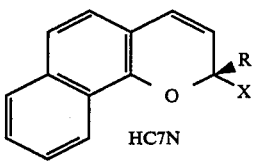

HC7N

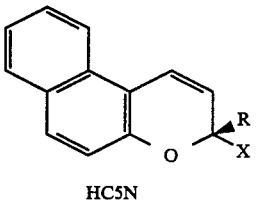

HC5N

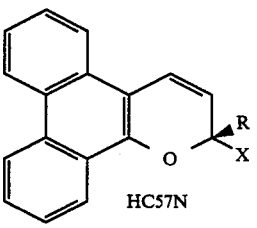

HC57N

Figure 1:
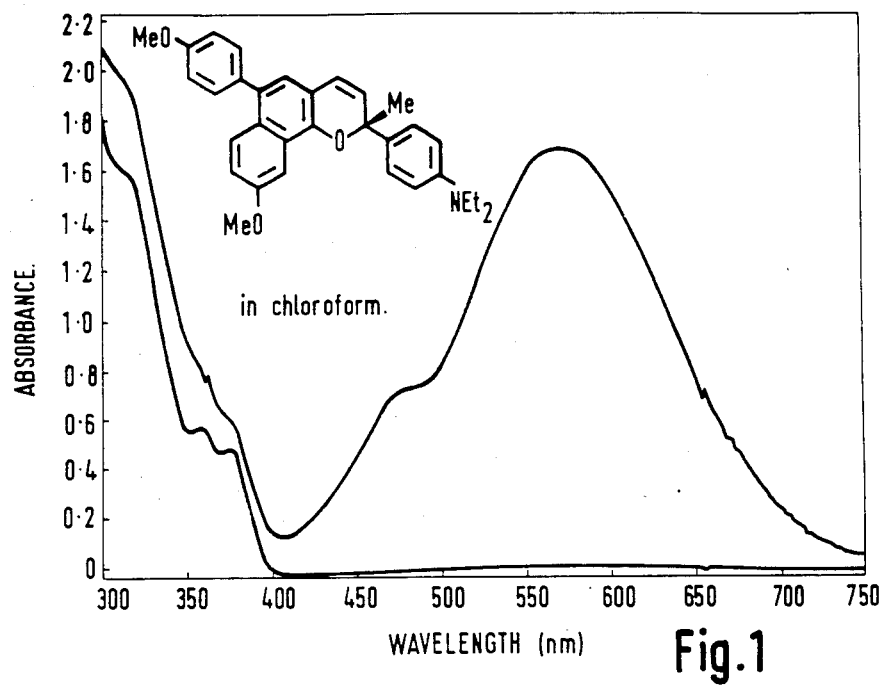
FIGS. 1 to 8 represent qualitative spectra of various materials formed in accordance with the present invention.

In the above formulae, R is an alkyl or aryl group and X represents an aryl group having a itrogen-containing substituent. The group represented by R may also be an aryl group having a nitrogen-containing substituent.

R is preferably lower alkyl, e.g. methyl, ethyl or propyl or phenyl and X is preferably a phenyl group having a nitrogen-containing substituent in the ortho or para position, e.g. a primary, secondary or tertiary amino, morpholino, piperidino, pyridino, pyrazolino or pyrrolidino group. However, R may also represent a phenyl group having a similar nitrogen-containing substituent in the ortho- or para position.

In the case where the aryl group represented by R or X has a heterocyclic ring nitrogen substituent in the ortho or para position, the heterocyclic substituent is bonded to the aryl group via the ring nitrogen atom.

The 'N' series of the heliochromic pyrans which are currently preferred are the HC7N series of compounds. A wide variety of substituents are possible in the benzo-pyran and naphthopyran rings of these compounds. For example, if we consider the compounds of the HC7N series having the following general formula:

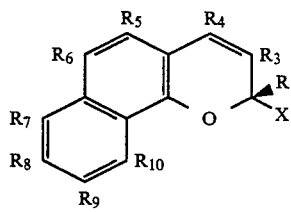

the positions represented by $R_3$ to $R_{10}$ can be selected from hydrogen, alkyl, (preferably lower alkyl, i.e. 1 to 5 carbon atoms), aralkyl, aryl (including substituted phenyl), alkoxy, hydroxy, alkyl- or dialkyl-amino, alkylamino-phenyl, halogen or heterocyclic groups, with the proviso that $R_3$ or $R_4$ is not alkoxy, hydroxy or alkyl- or dialkylamino. Examples of heterocyclic groups are furyl or thienyl groups.

Preferably $R_3$ and $R_4$ are both hydrogen since substituents in these positions can cause undesirable steric interactions in the coloured form produced on opening the pyran ring. Substitution in the positions other than the $R_6$ position has little influence on the photochromic behaviour of the compounds.

However, substitution in the $R_6$ position has a significant influence on the photochromic behaviour of the compounds. For example, the introduction of an electron-releasing group as a substituent in the $R_6$ position will produce a bathochromic shift in the absorption spectra of the coloured form. Examples of such substituents are alkylamino, dialkylamino, aminophenyl, alkoxy, alkoxy phenyl or alkyl- or dialkylamino-phenyl.

The HC7N series of compounds show a heliochromic response from colourless to blue or purple/blue in sunlight, depending on the solvent or plastics matrix in which the compound is held. Thermal fade properties of the HC7N compounds ar4e generally suitable for use in sunglasses and bleaching efficiencies in diffuse daylight at ambient temperatures appears to be higher than those of the corresponding HC7 compounds. In addition, fatigue resistance is good and the compounds can be incorporated into plastics lenses by the imbibition technique described in our above copending patent application. In principle any plastics material having the desired optical properties may be used for the matrix of the lenses in accordance with this invention. Examples include polycarbonate and alkyl acrylate and methacrylate lenses. The most commonly used material for plastic lenses is diethylene glycol bis(allyl carbonate) usually known as CR-39 (CR-39 is a trade mark of P.P.G.Ltd.). Methods of manufacturing plastic lenses are described for example in U.S. Pat. Nos. 3,944,637; 2,542,386 and 3,404,861, the disclosure of which are incorporated herein by reference.

Many of the nitrogen containing pyran compounds which are described in broad terms by the HC1N, HC7N etc. series are novel chemical compounds.

According to another aspect of this invention, therefore, there is provided a heliochromic pyran having the general formula (IIA):

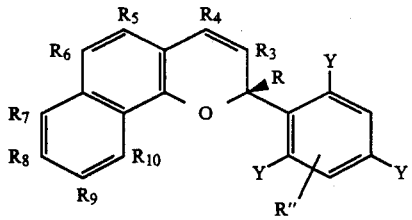 (IA)

wherein R$_3$ to R$_{10}$ have the significance indicated above, R is alkyl, R' represents one or more substituents independently selected from hydrogen, alkyl, halogen, alkoxy, aryl, or a heterocyclic group and each Y independently represents hydrogen, amino or alkyl- or dialkyl amino or a nitrogen-containing heterocyclic group, with the proviso that at least one of Y is a nitrogen-containing group, and wherein the ring containing the substituent R' may be benzannelated. Examples of heterocyclic groups are furyl, thienyl and pyrryl.

The invention also includes heliochromic pyrans having the general formula:

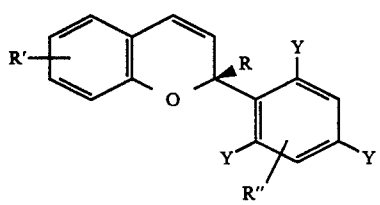 (IIA)

in which R, R" and Y have the same significance as above in formula (IIA), and R' represents one or more substituents independently selected from hydrogen. Alkyl, halogen, alkoxy, aryl, amino or substituted amino or a heterocyclic group (such as furyl or thienyl)).

It is also possible to prepare a series of bis-benzopyran compounds which also colour to blue. Such compounds show promising behaviour in terms of improved resistance to photodegradation. This may arise from an ability of the surviving benzopyran structure to continue to function after the first ring has been degraded. However, as the attached spectra will show the bis-benzopyrans do appear to offer the further advantage that their colourless forms absorb more strongly in the near ultra-violet than the coloured forms, thus increasing the conversion to the coloured form and reducing the internal filter effect.

The naphtho-bis-pyrans are also novel compounds and may be represented by the following general formula:

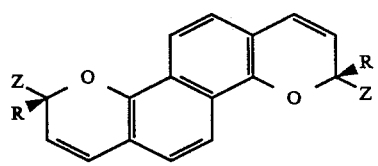 (III)

wherein R is an alkyl or aryl group and Z is hydrogen, alkyl or aryl, preferably at least one of R and Z is a phenyl group substituted with a primary, secondary or tertiary amino group or a heterocyclic nitrogen-containing group such as one of the heterocyclic nitrogen groups mentioned above. The naphthalene ring may contain substituents such as those represented by R$^1$ in formula (1A).

Synthesis of HC7N series of compounds

These compounds can be prepared by a modified Claisen rearrangement as described in our above copending patent application, by reacting the appropriate phenol with a propargyl alcohol derivative.

This modified Claisen rearrangement provides a general procedure for the preparation of pyran compounds, comprising heating a phenol with an appropriate propargyl derivative in a solvent in the presence of a suitable catalyst under mild reaction conditions.

In contrast with reaction conditions normally employed in Claisen rearrangements, the process is carried out at relatively low temperatures, e.g. in boiling xylene or toluene and in the presence of a suitable catalyst. Generally, the reaction temperature should not exceed about 180° C. and is preferably not more than 160° C. or less. The reaction can be expressed in general terms as follows:

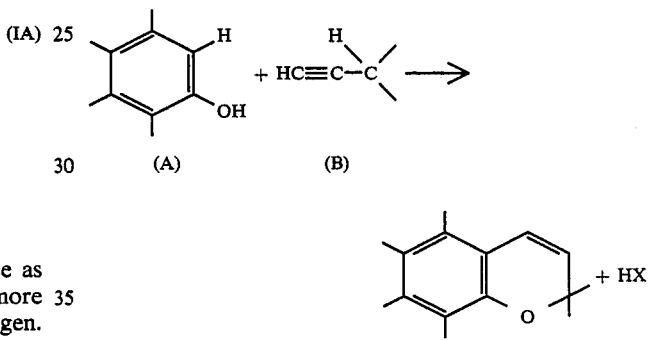

in which (A) can be any phenol and (B) a propargyl alcohol or propargyl alcohol derivative, such as a propargyl acetate. The reaction is catalysed by alumina and proceeds at relatively low temperatures with a marked absence of side reactions. In place of the acetate it is possible to use any aliphatic or aromatic carboxylate, e.g. the propionate or benzoate.

Improved yields are obtained using a propargyl acetate and heating this with a phenol in a solvent such as xylene in the presence of acidic alumina as catalyst. Surprisingly, these relatively mild conditions bring about a Claisen rearrangement whereas the traditional reaction conditions, e.g. heating to about 210° C. in strongly acid or base conditions, caused thermal decompositions of the reactants and/or desired product.

This process provides a convenient one-step synthesis of benzo- and naphthopyrans using any phenol and the appropriate propargyl alcohol or acetate or other propargyl alcohol derivative.

Propargyl acetates can be prepared by reacting an appropriate ketone with lithium acetylide. A lithium acetylide/ethylene diamine complex is added with stirring to a solution of the ketone in a suitable solvent, such as tetrahydrofuran or dimethyl sulphoxide. The product is the corresponding propargyl alcohol and the alcohol is conveniently converted to the acetate by reaction with acetyl chloride in a suitable solvent.

However, because of the difficulty in effecting an efficient conversion of the propargyl alcohol to the acetate and the subsequent separation of the latter, it is desirable to utilise the propargyl alcohol directly as a starting material.

The propargyl alcohol may be obtained by treating a ketone (which is substituted with a nitrogen-containing group in the ortho or para position) with a lithium acetylide/ethylene diamine complex in a suitable solvent. It has been found that yields are markedly improved if dry dimethyl sulphoxide is used as the solvent.

Figure 9:
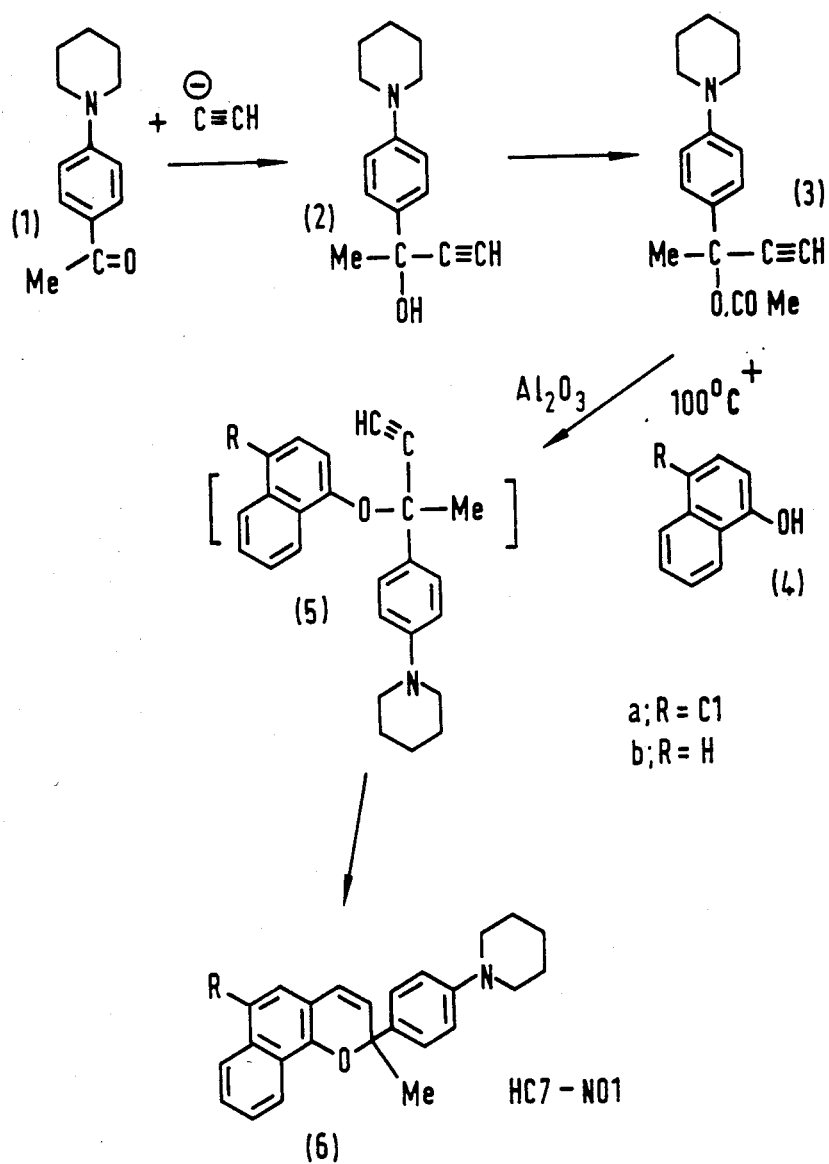
FIGS. 9 to 15 represent various reaction schematis in accordance with the present invention.

Preparation of the HC7N series of compounds in illustrated by the reactions shown in (FIG. 9 of the accompanying drawings). FIG. 9 shows the reactions resulting in the formation of the 2-p-piperidino-phenyl derivative of HC7, (hereinafter called HC7N-O1).

Referring to FIG. 9 p-piperidinoacetophenone (1) is treated with a lithium acetylide/ethylene diamine complex to yield the propargyl alcohol (2). The alcohol can be converted to the acetate (3) or reacted directly with 1-naphthol (4) in the presence of acidic alumina. The initial product is presumably the propargyl ether (5b) which spontaneously undergoes rearrangement to form HC7-NO1 (6).

Example 1
(See FIG. 9 of the accompanying drawings)

1-Naphthol (4b) (10 g) and a 45:55 mixture of the propargyl alcohol (2) and unreacted p-piperidinoacetophenone (1) (20 g) were dissolved in hot toluene (75 cm³) and the solution was adsorbed on to acidic activated alumina (200 g) packed in a chromatography column. Under these mild conditions, the propargyl alcohol (2) reacted with the 1-naphthol (4b) to give, presumably, the propargyl ether (5b), which spontaneously underwent a Claisen rearrangement to HC7-NO1 (6b). The product was eluted from the column with cold toluene. The photochromic fractions were combined, decolourised by boiling with activated charcoal (4 g), and evaporated. The residue was purified by chromatography on alumina using a 1:9 mixture of dichloromethane and hexane as eluant. HC7-NO1 (6b) was obtained as an oil which was shown to be nearly pure by n.m.r. spectroscopy. The impurity was a small amount of unreacted starting ketone (1).

Similar procedures can be employed to prepare other compounds in this series.

The following additional Examples are given to illustrate the preparation of further specific compounds of the HC7N series. In these Examples the structure of the naphthopyrans and the reaction equations are shown in the accompanying Figs.

Figure 10:
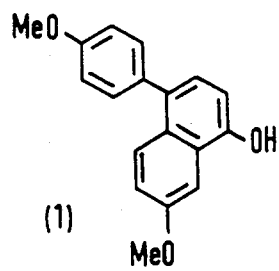
Figure 10:
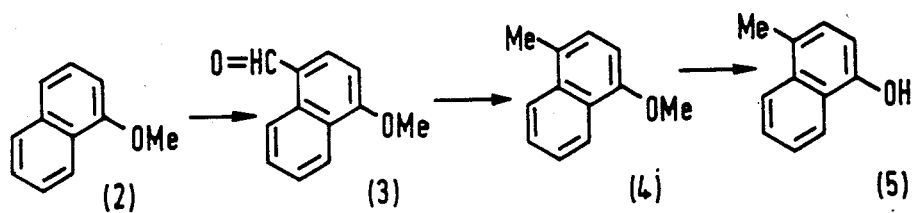
Figure 10:
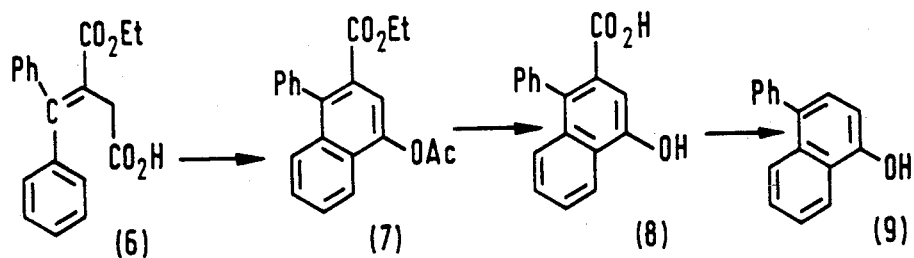
Figure 10:
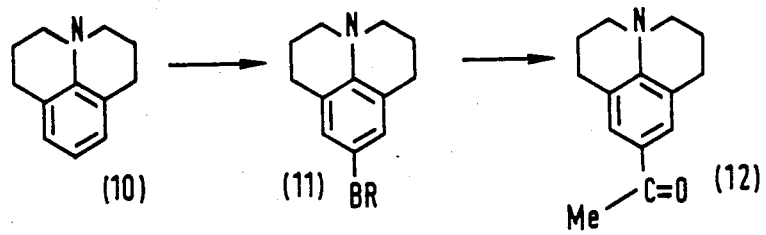
Figure 10:
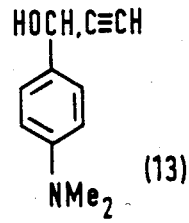

Preparation of substituted naphthol starting materials
4-Methyl-1-naphthol (5) (see FIG. 10 of the accompanying drawings)

Formylation

Phosphorus oxychloride (315 g, 1.6 mole) was added dropwise over 4 hours to a stirred solution of 1-methoxynaphthalene (250 g) (2) in dried dimethylformamide (150 g). the reaction mixture was heated on a water bath for a further 4 hours, cooled, and poured onto ice (1 k) and 2M aqueous sodium acetate (1.5 l). The organic layer was extracted with dichloromethane (1 l) and washed with dilute hydrochloric acid and then with water. The organic layer was dried (MgSO₄), filtered, and the solvent removed. 4-Methoxy-1-naphthaldehyde (3) was obtained as a pale yellow oil.

Reduction

4-Methoxy-1-naphthaldehyde (3) was dissolved in ethylene glycol (1 l) and hydrazine hydrate (125 g) was added. Potassium hydroxide (125 g) was added to the mixture which was heated at 200° C. for 5 hours. The reaction mixture was allowed to cool, poured onto ice (1 k), and treated with ether. A yellow solid separated which is assumed to be the hydrazide of the 4-methoxy-1-naphthaldehyde. The solid (85 g) was filtered off and the filtrate was separated. The ether layer was dried (MgSO₄), filtered and the solvent removed. The residual oil was 4-methyl-1-methoxynaphthalene (4).

Hydrolysis

4-Methyl-1-methoxynaphthalene (4) (145 g) was mixed with pyridine hydrochloride (250 g) and the mixture was heated at 200° C. for 3 hours. The mixture was cooled, treated with dilute hydrochloric acid, and extracted with ether. The ether extract was dried (MgSO₄), filtered and the solvent removed, leaving a black oil which was extracted with petroleum b.p. 60°–80° C. (4×100 cm³). 4-Methyl-1-naphthol (5) was obtained as near colourless oily crystals which darken on storage.

Figure 2:
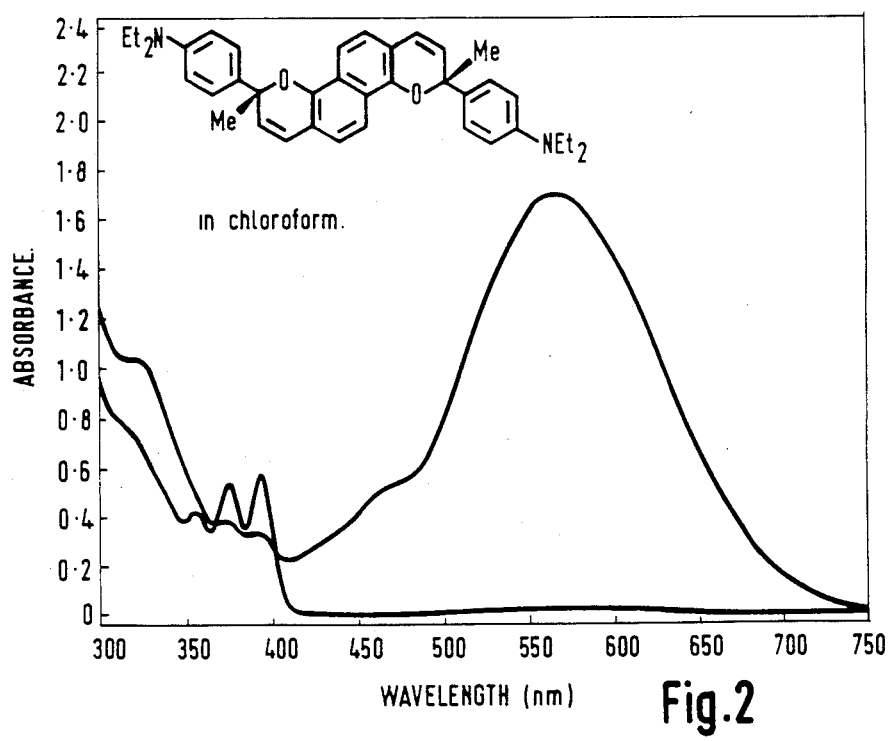

4-Phenyl-1-naphthol (9) (see FIG. 2 of the accompanying drawings)

Cyclisation

Diphenylmethylenesuccinic half ethyl ester (6) (100 g) was dissolved in acetic anhydride (250 cm³) and anhydrous sodium acetate (100 g) was added. The mixture was heated on a water bath for 6 hours, cooled and poured onto crushed ice (1 k). The mixture was extracted with dichloromethane (300 cm³), dried (MgSO₄), filtered, and the solvent removed.

Hydrolysis

The residual ester (7) was hydrolysed by boiling with 10% ethanolic potassium hydroxide solution (600 cm³) for 2 hours. Most of the ethanol was removed and the residue was acidified with 5M hydrochloric acid. The liberated oily acid (8) was extracted into chloroform (250 cm³), dried (MgSO₄), filtered, and the solvent removed. The residue was crystallised from acetone giving 4-phenyl-1-hydroxy-3-naphthoic acid (8) as a pale yellow solid.

Decarboxylation

The naphthoic acid (8) (20 g) was dissolved in quinoline (150 cm³) and copper bronze (20 g) was added. The mixture was boiled for 4 hours and left to cool. The mixture was filtered and the filtrate treated with 5M hydrochloric acid and extracted with chloroform. Work up gave a dark brown oil (7 g) which contained less than 20% 4-phenyl-1-naphthol (9). The failure of the decarboxylation stage is attributed to the quality of copper bronze used. Sufficient product was obtained to make the 6-phenyl-benzochromene (4D; R=Ph) (Sheet 3).

Acetyl derivative of Julolidine

Bromine (5 g 0.032 mole) was added dropwise with stirring to a solution of julolidine (10) (5 g. 0.03 mole) in chloroform. When the addition was complete, the mixture was stirred for 10 minutes.

The orange colour of the solution was discharged and a colourless solid separated. 1M Sodium bicarbonate solution (50 cm³) was added and the chloroform layer was separated, dried (MgSO₄), filtered and the solvent removed. The bromo-julolidine (11) was obtained as a pale yellow oil.

Bromo-julolidine (11) (7.8 g) was dissolved in dry tetrahydrofuran (100 cm$^3$) and cooled to −78° C. Under nitrogen, a solution of n-butyl lithium [(20 cm$^3$) of a 1.6M solution in hexane] was added, allowed to stir for 1 hour, and then N,N-dimethylacetamide (3.5 g) was added dropwise. The mixture was maintained at −78° C. for 10 minutes and allowed to warm to room temperature. The mixture was poured onto crushed ice, weakly acidified with 2M hydrochloric acid and extracted with ether (2×100 cm$^3$). The ether extract was dried (MgSO$_4$), filtered and the solvent removed, leaving a 2:3 mixture of acetyljulolidine (12) and unreacted bromo-julolidine (11) as a pale yellow oil.

Figure 11:
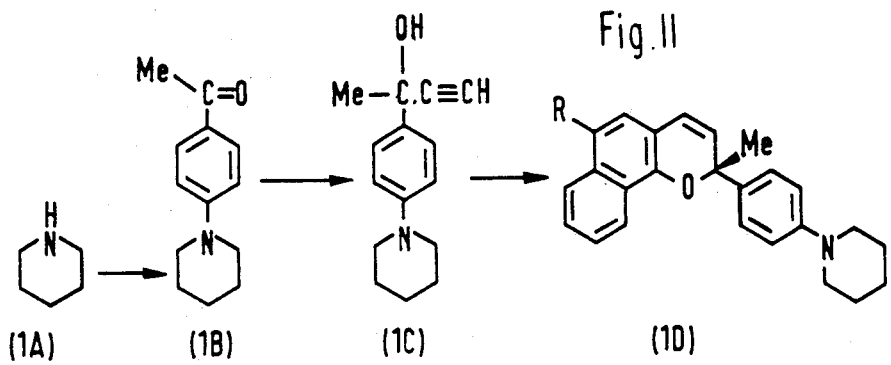
Figure 11:
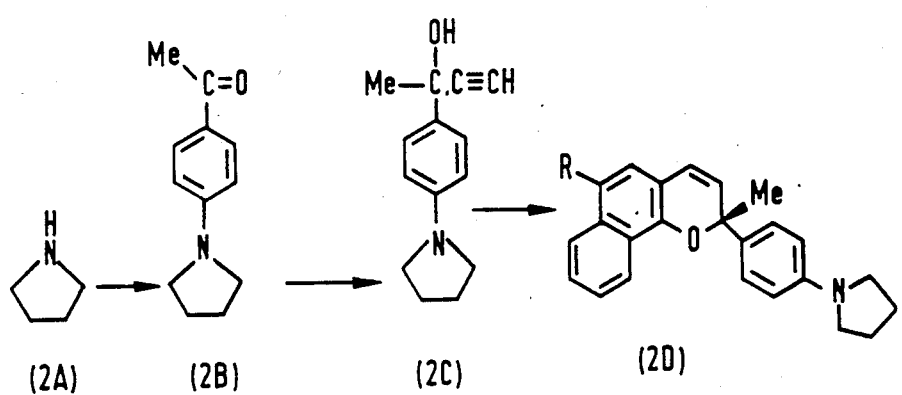
Figure 11:
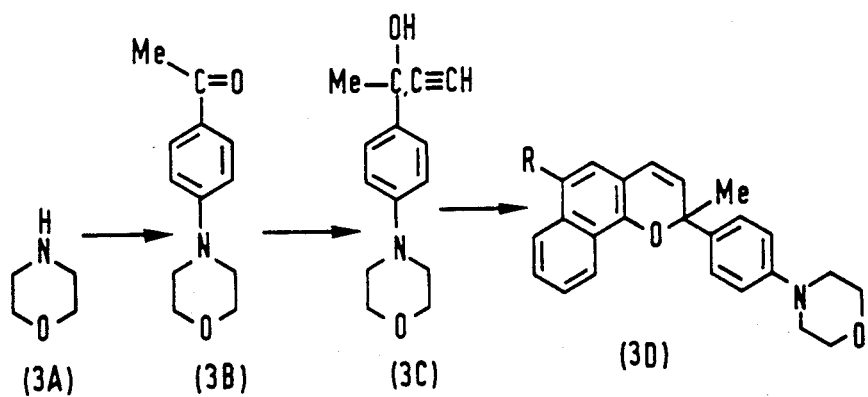
Figure 11:
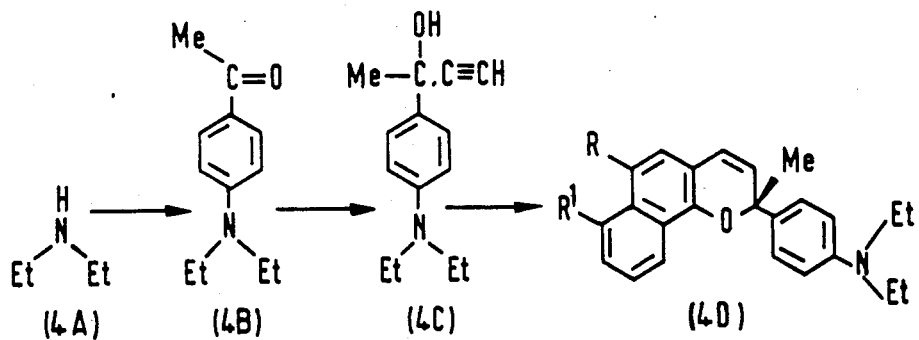

The preparation of substituted p-aminophenyl-acetylenic alcohols (FIG. 11 of the accompanying drawings)

3.1 General Procedure

The p-N-substituted aminophenyl ketone (1 part) is dissolved in dry dimethyl sulphoxide and the solution is heated to 60° C. Lithium acetylide/ethylene diamine complex (1 part) is added in portions to the stirred solution at such a rate that the temperature does not rise above 75° C. nor fall below 60° C. When the addition is complete, the reaction mixture is stirred at 60° C. for 3 hours and then poured onto crushed ice (6-8 parts). The reaction mixture is extracted with dichloromethane, the organic layer is separated, dried over anhydrous magnesium sulphate, and filtered, and the solvent removed from the filtrate. The residue is the acetylenic alcohol usually with a 90+% purity, based on analysis by n.m.r. spectroscopy. In the following examples, the residue, after removal of the solvent, was triturated with petroleum (b.p. 60°-80° C.). In some cases, the residual acetylenic alcohol solidified and was filtered off and washed with cold petroleum (b.p. 60°-80° C.). If the acetylenic alcohol failed to crystallise, petroleum was removed and the residual oil used directly.

3.1.1. 2-p-Morpholinophenylbut-3-yn-2-ol (3C) (see FIG. 11) p-Morpholinoacetophenone (3B) (30 g) was dissolved in dimethyl sulphoxide (100 cm$^3$) and lithium acetylide/ethylene diamine complex (30 g) was added in small portions to the solution at 60° C. so that the temperature did not rise above 75° C. Work up as described in the General Procedure described above, left the alcohol (3C) as a yellow solid (25 g, 80% yield).

3.1.2. 2-p-Diethylaminophenylbut-3-yn-2-ol (4C) (see FIG. 11)

Lithium acetylide/ethylene diamine complex (100 g) was added in small portions to a stirred solution of p-diethylamino-acetophenone (4B) (110 g) in dimethyl sulphoxide (300 cm$^3$) at 60° C. at a rate that the temperature did not rise above 75° C. Work up, as described in the General Procedure above, gave the alcohol (4C) as pale yellow plates (from petroleum b.p. 60°-80° C.) (125 g, 85% yield).

Figure 13:
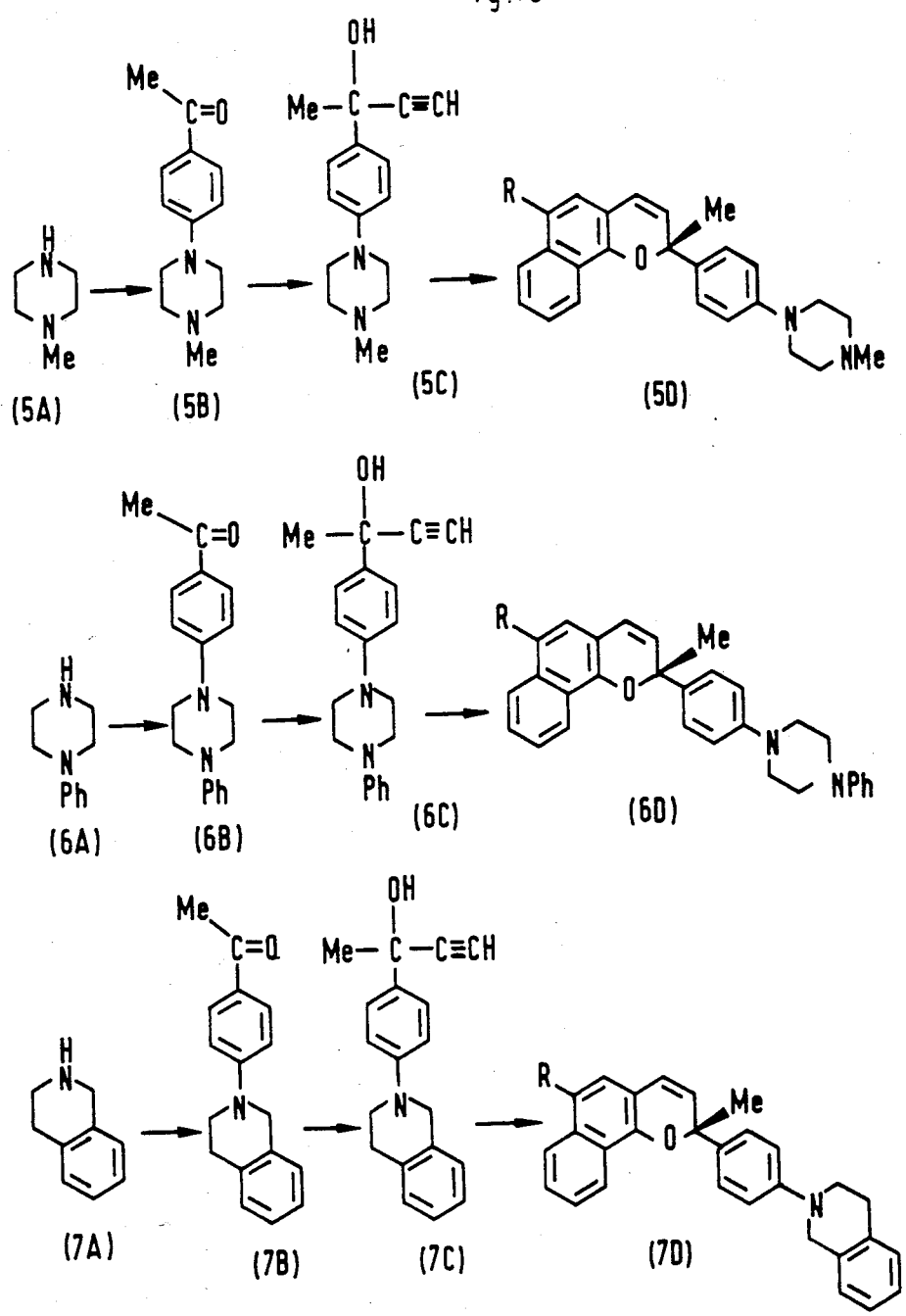

3.1.3. 2-p-N-Methylpiperazinophenylbut-3-yn-2-ol (5C) (see FIG. 13)

Lithium acetylide/ethylene diamine complex (25 g) was added in small portions to a stirred solution of p-N-methylpiperazino-acetophenone (5B) (25 g) in dimethyl sulphoxide (250 cm$^3$) at 60° C. at such a rate that the temperature did not rise above 75° C. Work up, as described in the General Procedure above, left the alcohol (5C) as a colourless powder (18 g, 67% yield (95%+purity).

3.1.4. 2-p-N-Phenylpiperazinophenylbut-3-yn-2-ol (6C) (see FIG. 13)

Lithium acetylide/ethylene diamine complex (38 g) was added in small portions to a stirred solution of p-N-phenylpiperazino-acetophenone (6B) (38 g) in dimethyl sulphoxide (380 cm$^3$) at 60° C. at such a rate that the temperature did not rise above 75° C. Work up, as described in the General Procedure above, left the alcohol (6C) as a yellow powder (27 g, 68% yield (90%+purity).

3.1.5. 2-p-(1,2,3,4-Tetrahydro-2-isoquinolinophenyl)-but-3-yn-2-ol (7C) (see FIG. 13)

Lithium acetylide/ethylene diamine complex (25 g) was added in small portions to a stirred solution of p-1,2,3,4-tetrahydroisoquinolineacetophenone (7B) (25 g) in dimethyl sulphoxide (250 cm$^3$) at 60° C. at such a rate that the temperature did not rise above 75° C. Work up, as described in the General Procedure above, left the alcohol (7C) in near quantitative yield as a gum (22 g) 90+% purity.

Figure 14:
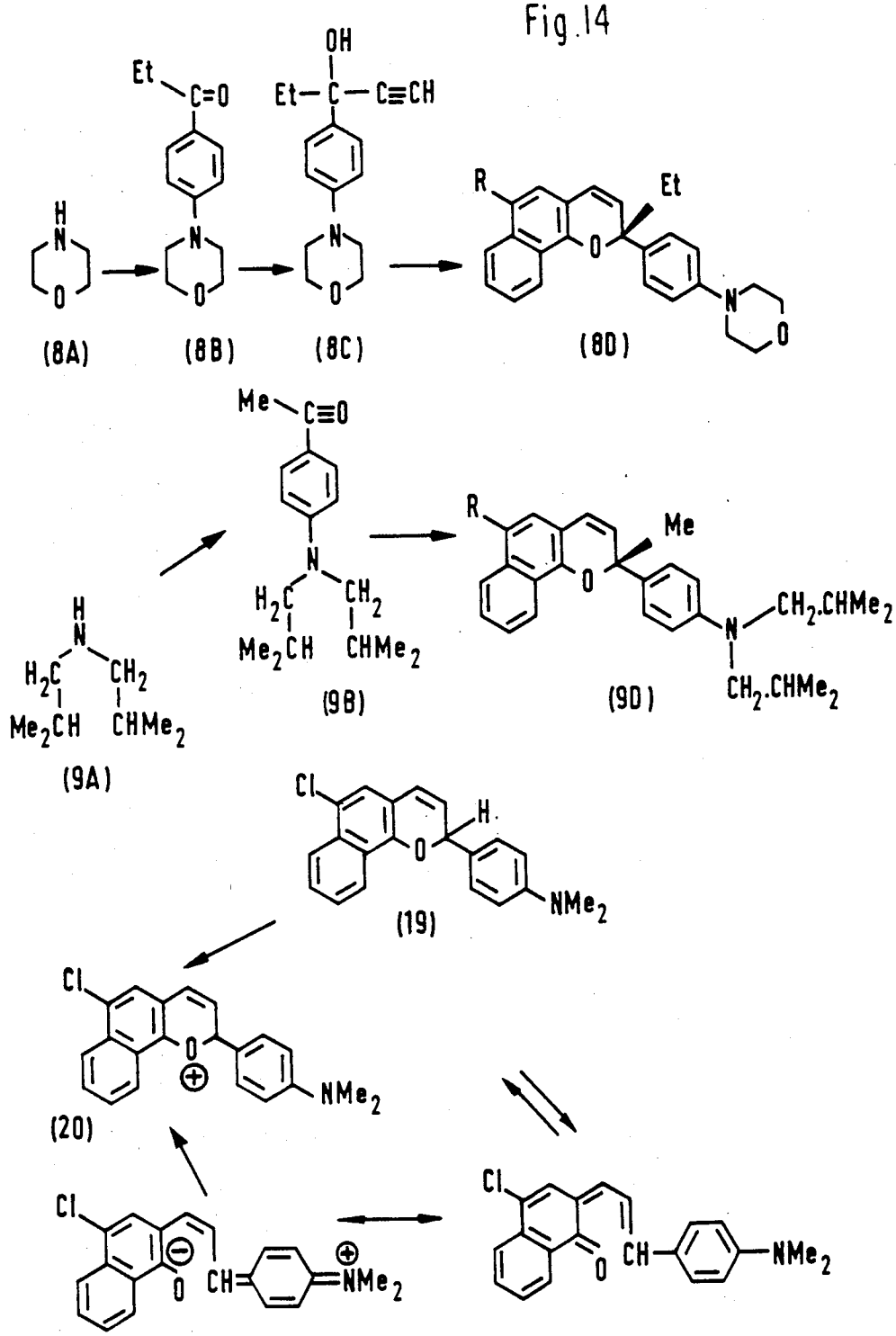

3.1.6 3-p-Morpholinophenylpent-1-yn-3-ol (8C) (see FIG. 14

Lithium acetylide/ethylene diamine complex (20 g) was added in small portions to a stirred solution of p-morpholinopropiophenone (8B) (20 g) in dimethyl sulphoxide (100 cm$^3$) at 60° C. at such a rate that the temperature did not rise above 75° C. Work up, as described in the General Procedure above, left the alcohol (8C) as an oil (21 g, 92% yield), 95+% purity.

3.1.7 p-Dimethylaminophenylpropynol (13) (see FIG. 10)

Lithium acetylide/ethylene diamine complex (20 g) was added in portions to a stirred solution of p-dimethylaminobenzaldehyde (20 g) dissolved in dimethyl sulphoxide (80 cm$^3$). When addition was complete was complete, the mixture was stirred for 30 minutes and then heated on a water bath for 15 minutes, and cooled. Work up, as described in the General Procedure above, left the alcohol (13) as a pale yellow oil (17 g, 71% yield).

The preparation of naphthopyrans of the HC7-N series (Refer to FIG. 11 of the accompanying drawings)

Example 2

6-Chloro-2-methyl-2-p-morpholinophenylbenzochromene (3D; R-Cl) (FIG. 11)

A hot solution of 2-p-morpholinophenylpropargyl alcohol (3C) (3 g) and 4-chloro-1-naphthol (3 g) in toluene (75 cm$^3$) was passed down a column of acidic alumina (100 g). The column was stripped using chloroform and the chloroform solution evaporated. The residual oil was purified by column chromatography on alumina, using dichloromethane and petroleum b.p. 60°-80° C. (1:20) as eluant. The heliochromic fraction was separated and the solvent removed. Recrystallisation of the residue from petroleum gave the chromene (3D; R=Cl) as a near colourless powder.

Example 3

2,6-Dimethyl-2-morpholinophenylbenzochromene (3D; R=Me) (FIG. 11)

2-p-Morpholinophenylpropargyl alcohol (3C) (8 g) and 4-methyl-1-naphthol (5 g) were dissolved in hot toluene (300 cm$^3$) and the solution added to dry acidic alumina (200 g) in a flask fitted with a condenser. The mixture was heated (20 minutes) on a water bath, cooled and filtered. The residual alumina was extracted with chloroform (3×100 cm³). The combined organic filtrates and extracts were evaporated and the residual oil was purified by chromatography on acidic alumina (100 g) using a 1:20 mixture of dichloromethane and petroleum as eluant. The heliochromic fraction was separated and the solvent removed, leaving a dark brown oil. Two further chromatographic separations failed to improve the quality of the benzochromene (3D; R=Me). The brown oil darkens in air but its n.m.r. spectrum indicates less than 5% impurities.

Example 4

2,6-Dimethyl-2-p-diethylaminophenylbenzochromene (4D; R=Me) (FIG. 11)

Figure 7:
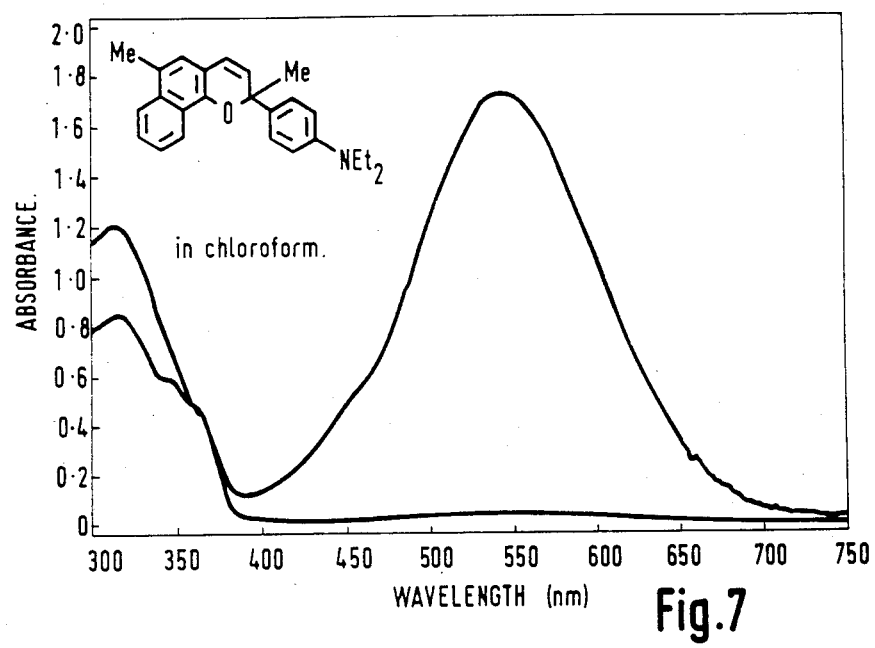

A hot solution of 2-p-diethylaminophenylpropargyl alcohol (4C) (15 g) and 4-methyl-1-naphthol (10 g) in toluene (200 cm³) was passed down a column of dry acidic alumina (300 g). The heliochromic fraction was eluted with dichloromethane and the solvent removed. The residual oil was purified by chromatography on acidic alumina (300 g) using a solution of dichloromethane and petroleum (1:20) as eluant. The heliochromic fraction was evaporated and the residual colourless oil was crystallised from petroleum giving the chromene (4D; R=Me R¹=H) as nearly colourless crystals. The qualitative spectrum in chloroform before and after exposure to a flash gun is shown in FIG. 7.

Example 5

6-Phenyl-2-methyl-2-p-diethylaminophenylbenzochromene (4D; R=Ph) R¹=H (FIG. 11)

Figure 8:
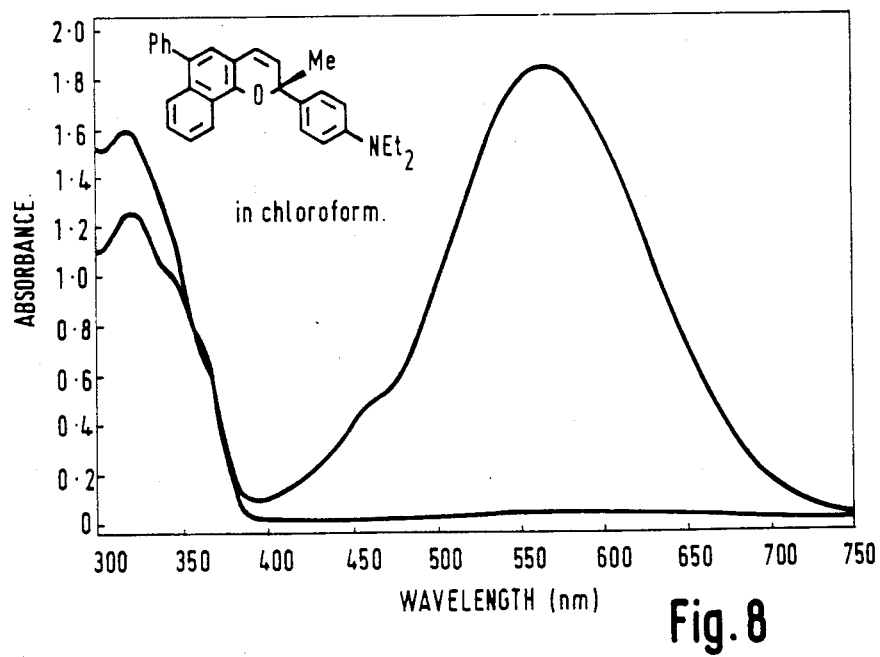

4-Phenyl-1-naphthol (5 g) and 2-p-diethylaminophenylpropargyl alcohol (4C) (5 g) were dissolved in toluene (200 cm³) and acidic alumina (100 g) was added. The reaction mixture was heated at 100° C. for 10 minutes, cooled slightly, and filtered. The alumina residue was washed with acetone (3×200 cm³) and the toluene filtrate and acetone extracts were combined. The solvent was removed and the residual oil was cleaned up by flash chromatography on alumina (400 g) using a 1:3 mixture of ether and petroleum b.p. 60° C. as eluant. Solvent was removed and the residue was then carefully purified by column chromatography on alumina (200 g) using petroleum (b.p. 40° C.) as eluant. The heliochromic fraction was evaporated and the residue was recrystallised from a 1:9 mixture of chloroform and petrol (b.p. 40°–60° C.). The product showed a colourless to purple-blue heliochromic response. The qualitative spectrum in chloroform before and after exposure to a flash gun is shown in FIG. 8.

Example 6

Figure 12:
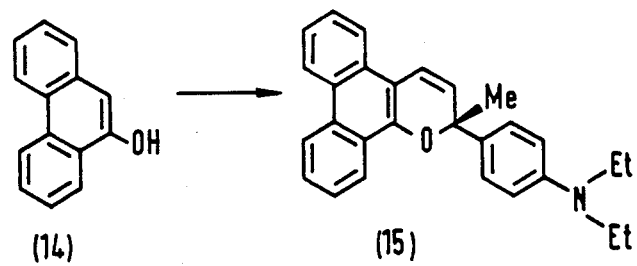
Figure 12:
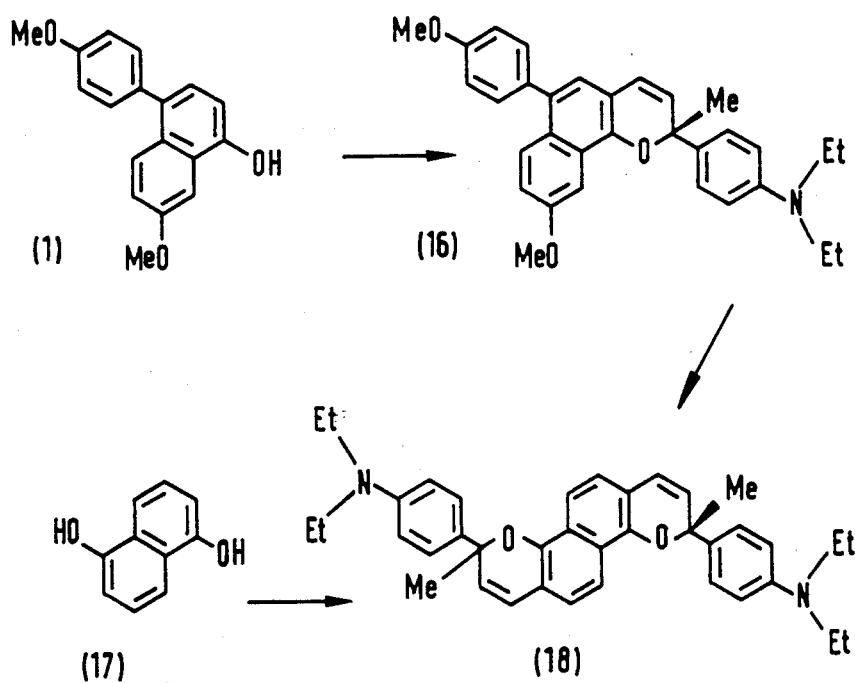

5,6-Benzo-2-methyl-2-p-diethylaminobenzochromene (15) (FIG. 12)

A hot solution of 9-phenanthrol (14) (1.7 g) and 2-p-diethylaminophenylpropargyl alcohol (4C) (2.5 g) in toluene (30 cm³) was poured onto a column of dry acidic alumina (75 g). The heliochromic material was eluted with chloroform. Solvent was removed and the residual oil was purified by chromatography on acidic alumina (75 g) using a solution of dichloromethane and petroleum (1:20) as eluant. Removal of solvent left a pale yellow oil which, on crystallisation from petroleum, gave the benzochromene (15) as pale yellow crystals.

Example 7

6-p-Methoxyphenyl-9-methoxy-2-methyl-2-p-diethylaminobenzochromene (16) (FIG. 12)

A hot solution of 7-methoxy-4-(p-methoxyphenyl)-1-naphthol (1) (1.5 g) and 2-p-diethylaminophenylpropargyl alcohol (4C) (3 g) in toluene (30 cm³) was poured onto a column of dry acidic alumina (75 g) and worked up as described in the previous example. The benzochromene (16) was obtained as a near-colourless powder.

Example 8

2-methyl-2-p-diethylaminophenyl-1,5-bisbenzochromene (18) (FIG. 12)

1,5-Dihydroxynaphthalene (17) (10 g) was suspended in hot toluene (350 cm³) and p-diethylaminophenylpropargyl alcohol (4C) (25 g) added. Acidic alumina (400 g) was then added and the mixture was heated (10 minutes) with occasional shaking, on a water bath. Alumina was filtered off and extracted with acetone (2×200 cm³). The filtrate and extracts were evaporated and the residual highly coloured oil was purified by chromatography on acidic alumina (100 g). The column was first eluted with ether which removed the main coloured impurities and then with dichloromethane and petroleum mixture (1:10). The heliochromic fraction gave a pale yellow oil which solidified to give a pale yellow powder of the "1,5-bisbenzochromene" (18).

Example 9

Figure 15:
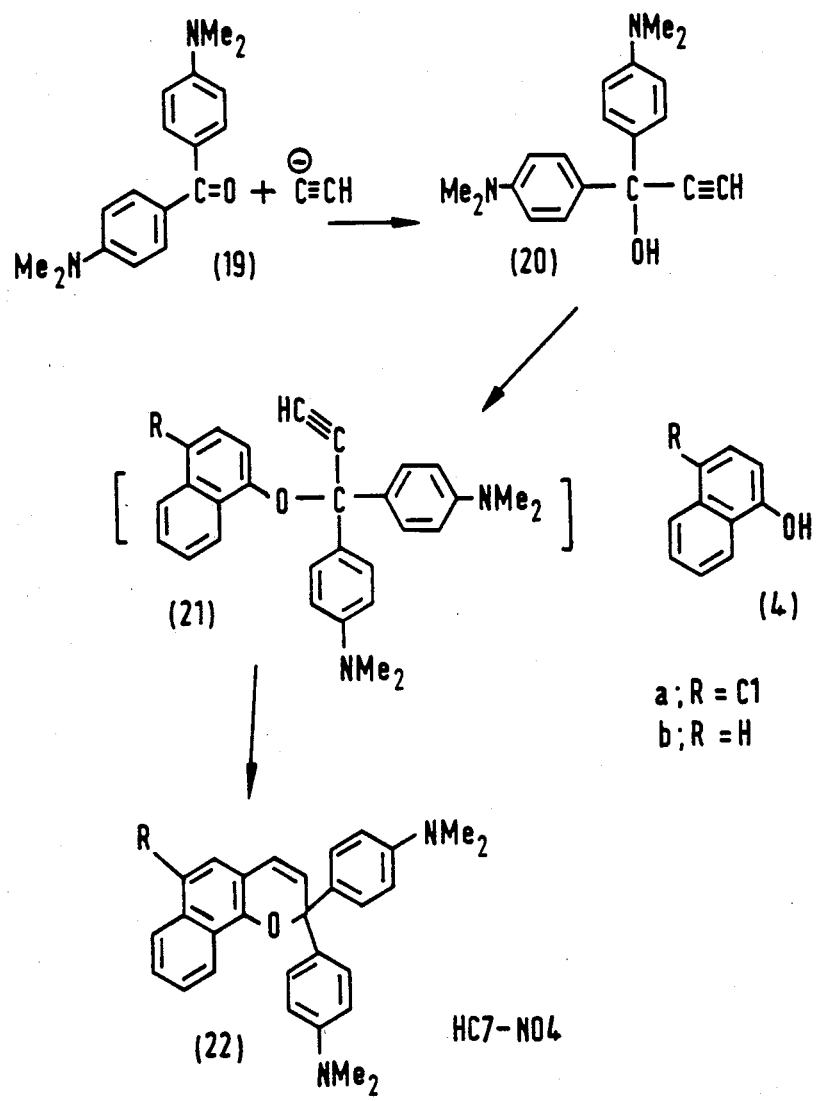

6-Chloro-2,2'-bis-p-dimethylamino-benzochromene(22) (FIG. 15)

Mischler's ketone (19) (25 g) in tetrahydrofuran was treated with sodium acetylide (18 g) as a slurry in xylene. The mixture was boiled for 3 hours. Work up gave mainly unrecovered ketone but the residual oil and 4-chloro-1-naphthol (4a) were dissolved in toluene and added to a column of acidic alumina. An intense blue colouration was observed when subjected to AM2 radiation which was not given by Mischler's ketone (19) and 4-chloro-1-naphthol (4a) under similar conditions and presumably was due to the presence of the benzochromene (22, R=Cl).

Example 10

2-Methyl-2-pyrrolidonophenylbenzochromene (2D; R=H) (FIG. 11)

p-Pyrrolidinophenylpropargyl alcohol (2C) (2.5 g) and 1-naphthol (3 g) were dissolved in toluene (50 cm³) and the solution passed down a column of acidic alumina (150 g), using toluene as eluant. The deep purple fraction was washed with dilute hydrochloric acid to remove the more basic coloured impurities, dilute sodium hydroxide, and then with water. The toluene solution was dried and evaporated under reduced pressure and the residue chromatographed again on acidic alumina (100 g) using a 5:1 mixture of cyclohexane and dichloromethane as eluant, to give the benzochromene (2D; R=H) as a colourless oil.

Example 11

6-Chloro-2-methyl-2-p-pyrrolidinophenylbenzochromene (2D; R=Cl) (FIG. 11)

A solution of p-pyrrolidinophenylpropargyl alcohol (2C) (5 g) and 4-chloro-1-naphthol (5 g) in toluene (75 cm³) was passed down a column of acidic alumina (100 g), using toluene as eluant. The colourless but heliochromic fraction (which turned blue on exposure to light from a flashgun) was evaporated and the residual solid recrystallised from acetone. The first crop of pure near colourless crystals was the benzochromene (4D; R=Cl).

Example 12

2-Methyl-2-p-morpholinophenylbenzochromene (3D; R=H) (FIG. 11)

Figure 5:
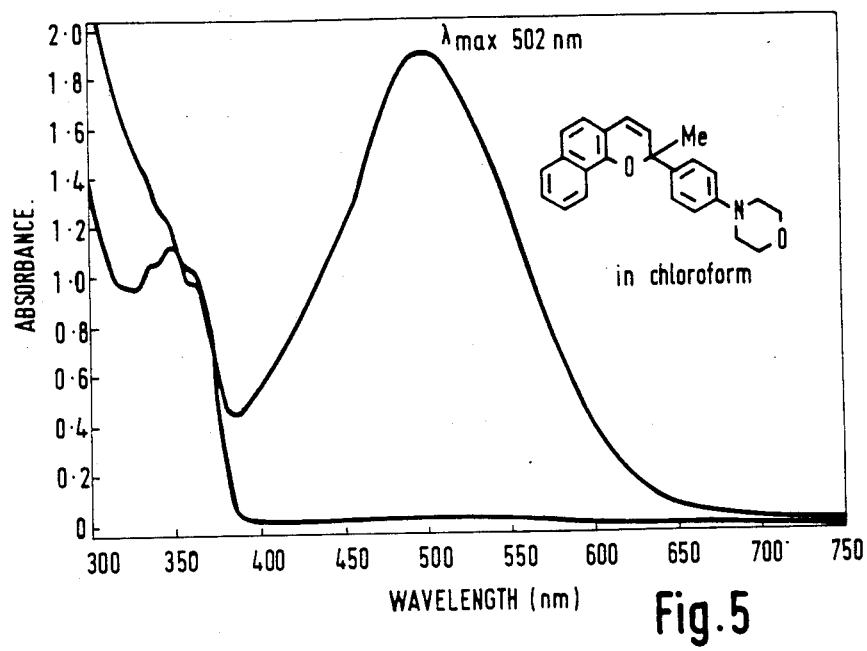

A solution of 2-p-morpholinopropargyl alcohol (3C) (3.5 g) and 1-naphthol (4 g) in toluene (50 cm³) was passed down a column of acidic alumina (150 g), using toluene as eluant. Chromatography and work up, as before, gave the benzochromene (3D; R=H) as colourless crystals from chloroform and cyclohexane. Its qualitative spectrum in chloroform before and after exposure to a flash gun is shown in FIG. 5.

Example 13

6-Chloro-2-methyl-2-p-diethylaminophenylbenzochromene (4D; R=Cl) (FIG. 11)

A solution of 2-p-diethylaminophenylpropargyl alcohol (4C) (10 g) and 4-chloro-1-naphthol (10 g) was dissolved in toluene (150 cm³, warmed to 80° C. and passed down a column of acidic alumina (200 g), using dichloromethane (200 cm³ as eluant. The heliochromic fraction was separated and the solvent removed. The residue was chromatographed on acid alumina (300 g), using 1:9 mixture of dichloromethane and petroleum (b.p. 60°–80° C. as eluant). The heliochromic first fraction was separated and on evaporation gave a first crop of the benzochromene (4D; R=Cl).

Example 14

2-Methyl-2-p-diethylaminophenylbenzochromene (4D; R=H) (FIG. 11)

A solution of 2-p-diethylaminophenylpropargyl alcohol (4C) (10 g) and 1-naphthol (10 g) in toluene (150 cm³) were passed down a column of acidic alumina (150 g). Work up, as described above, gave a first crop of the benzochromene (4D; R=H).

Example 15

6-Chloro-2-methyl-2-p-(N-phenylpiperazinylphenyl)-benzochrome (FIG. 13) (6D; R=Cl)

Figure 4:
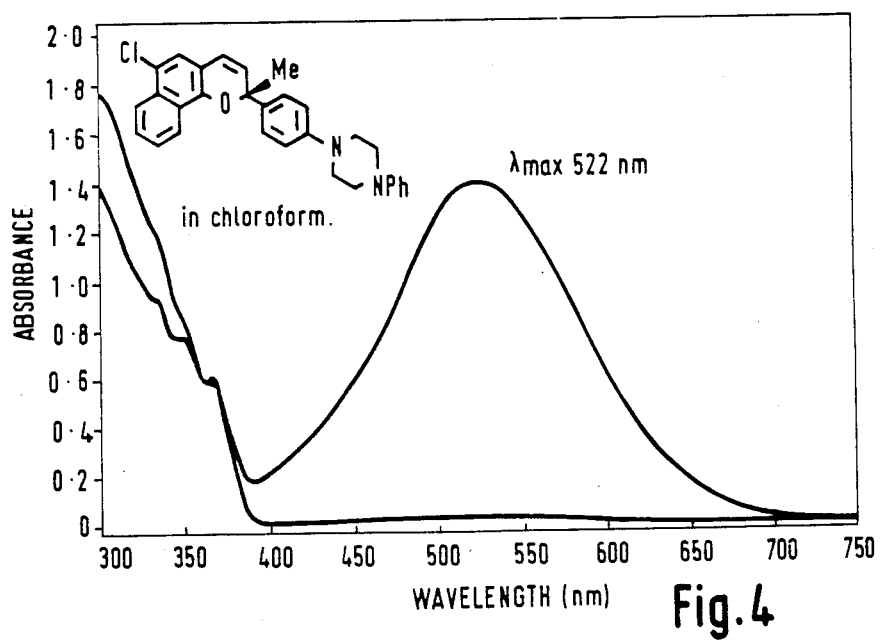

N-Phenylpiperazinylphenylproargyl alcohol (6C) (10 g) and 4-chloro-1-naphthol (5 g) were dissolved in hot toluene (200 cm³) and acidid alumina (150 g) was added. The mixture was heated (1 h) on a water bath, cooled and filtered. The alumina residue was extracted with acetone (4×200 cm³). The filtrate and extracts were combined and the solvent removed. The residue was purified by column chromatography using acidic alumina (150 g) and a 1:2 mixture of ether and petroleum as eluant. The benzochromene (6D; R=Cl) recrystallised from a 1:2 mixture of ether and petroleum as the ether evaporated slowly, giving pale yellow crystals (6.5 g, 46% yield). Its qualitative spectrum in chloroform before and after exposure to a flash gun is shown in FIG. 4.

Example 16

2,6-Dimethyl-2-p-(N-phenylpiperazinylphenyl)benzochromene (FIG. 11) (6D; R=Me)

Figure 3:
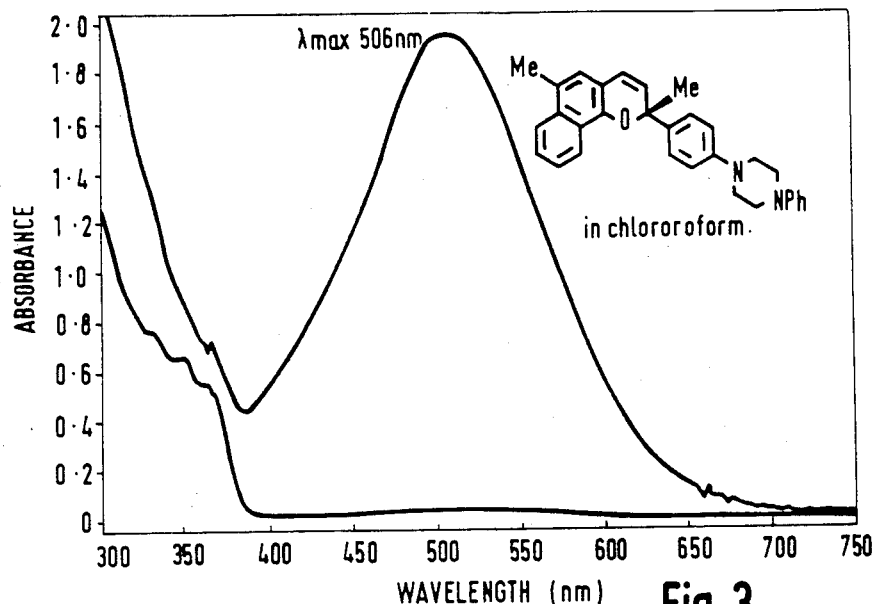

N-Phenylpiperazinylphenylpropargyl alcohol (6C) (8 g) and 4-methyl-1-naphthol (5 g) were dissolved in toluene (200 cm³) and acidic alumina (150 g) was added. The mixture was heated (1 h) on a water bath, cooled and filtered. Work up, as above, gave the benzochromene (6D; R=Me) as pale yellow plates (from a 1:2 mixture of ether and petroleum (3.5 g, 32% yield). Its qualitative spectrum in chloroform before and after exposure to flash gun is shown in FIG. 3.

Example 17

6-Chloro-2-methyl-2-p-(1,2,3,4-tetrahydro-2-isoquinolinylphenyl)benzochromene (7D; R=Cl) (FIG. 13)

(1,2,3,4-Tetrahydro-2-isoquinolinyl)phenylpropargyl alcohol (7C) (3 g) and 4-chloro-1-naphthol (3 g) were dissolved in toluene (100 cm³) and acidic alumina (50 g) added. The mixture was heated (5 minutes) on a water bath, cooled and filtered. The alumina residue was washed with acetone (3×100 cm³) and the filtrate and extracts were combined and the solvent removed under reduced pressure. The residue was purified by column chromatography on acidic alumina, using petroleum b.p. 40°–60° C. as eluant. The chromene was obtained as a pure pale yellow oil (0.7 g) which darkened on storage in the dark.

Example 18

2-Ethyl-6-methyl-2-p-morpholinophenylbenzochromene (8D; R=Me) (FIG. 14)

3-Morpholinopentyn-3-ol (8C) (7 g) and 4-methyl-1-naphthol (5 g) were dissolved in toluene (200 cm³) and acidic alumina (200 g) was added. The mixture was heated (35 minutes) on a water bath, cooled and filtered. The residue was washed with acetone (5×50 cm³). The filtrate and the extracts were combined and the solvent was removed. The residue was purified by column chromatography on alumina (200 g) using a 1:2 mixture of ether and petroleum b.p. 40°–60° C. as eluant. The benzochromene (8D; R=Me) was obtained as a pure pale yellow oil (2.8 g) which cannot be induced to crystallise and has darkened on standing in the dark.

Example 19

6-Chloro-2-p-dimethylaminophenylbenzochromene (19) (FIG. 14)

Figure 6:
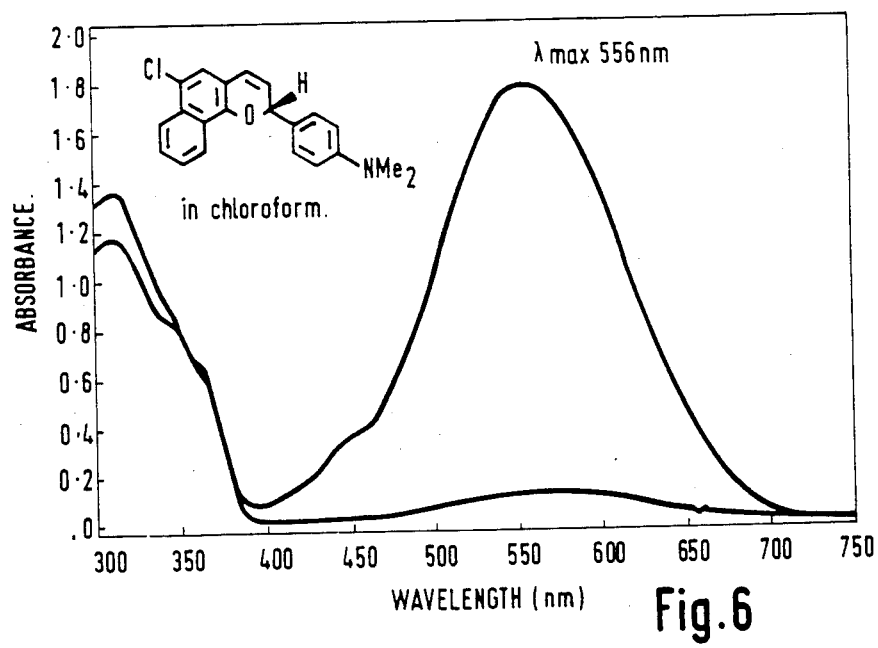

The above compound was prepared in analogous manner to that described in Example 13. The crude product from that reaction (5 g) was purified by careful column chromatography using neutral alumina (100 g) and a mixture of ether and light petroleum as eluant. The chromene (19) was obtained as near colourless crystals (20 mg) which colours rapidly on exposure to light. Its qualitative spectrum in chloroform before and after exposure to a flash gun is shown in FIG. 6. The photocoloured form fades much more slowly than the 2-methyl homologue.

Example 20

6-Chloro-2-methyl-2-(N-methylpiperazinylphenyl)-benzochromene (5D; R=Cl) (FIG. 13)

N-Methylpiperazinylphenylpropargyl alcohol (5C) (3 g) and 4-chloro-1-naphthol (5 g) were dissolved in hot toluene (150 cm³) and acidic alumina (100 g) was added. The mixture was heated (45 minutes) on a water bath and cooled. Glacial acetic acid (50 cm³) was added and the alumina was filtered off and washed with a 1:19 mixture of acetic acid in acetone (5×100 cm³). The filtrate and extracts were combined and organic solvents removed under reduced pressure using a rotatory evaporator. The residual oil was purified by column chromatography on acidic alumina (200 g) using a 1:2 mixture of ether and petroleum (b.p. 40°–60° C.) as eluant. The benzochromene (5D; R=Cl) was obtained as a pure, near colourless oil (0.3 g) which could not be induced to crystallise.

Example 21

Preparation of 2-methyl-7-methoxy-2-p-diethylaminophenylbenzochromene (4D; R=H, R¹=OMe) (FIG. 11)

A solution of 2-p-diethylaminophenylpropargyl alcohol (4C) (19.5 g, 0.05 mole) and 5-methoxy-1-naphthol (15 g, 0.09 mole) were dissolved in toluene (250 cm³) and heated on a water bath. The hot solution was passed down a column of dry acidic alumina (400 g) and eluted with toluene until the eluant was no longer photochromic. Toluene was removed and the residue was chromatographed on acidic alumina (300 g) using petrol (b.p. 60°–80° C.) and ether as eluant. The discoloured solid, after removal of the solvent, was further purified by chromatography on acidic alumina (150 g) using petroleum (b.p. 60°–80° C.) as eluant. Removal of the solvent left a solid which was recrystallised from petroleum (b.p. 60°–80° C.) giving the desired chromene as pale yellow crystals.

The absorption spectra of the coloured forms of the HC7 series of compounds depends largely on the nature of the substituent group in the 2-position. Generally, the HC7N compounds are blue to blue/purple.

In the following Table the colours of the various specific HC7N compounds are given. For comparison, data for two non-nitrogen compounds are given (compounds A and B in the Table).

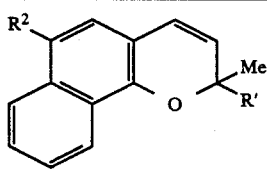

COLOURS OF HC7N COMPOUNDS
(for solutions in chloroform)

| Compound or Example No. | | | | |
|---|---|---|---|---|
| A | Me | Cl | yellow | 444 |
| B | Ph | Cl | orange | 464 |
| 12 | Morpholino | H | purple | 504 |
| 2 | Morpholino | Cl | blue-purple | 518 |
| 1 | Piperidino | H | blue-purple | 525 |
| — | Piperidino | Cl | purple-blue | 536 |
| 10 | Pyrrolidino | H | blue | 554 |
| 11 | Pyrrolidino | Cl | blue | 574 |
| 14 | Diethylamino | H | blue | 552 |

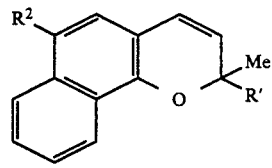

COLOURS OF HC7N COMPOUNDS
(for solutions in chloroform)

| Compound or Example No. | | | | |
|---|---|---|---|---|
| 13 | Diethylamino | Cl | blue | 574 |

The nitrogen-containing benzochromenes can be incorporated into the usual type of plastics lenses, such as polymers of alkyl methacrylates and polycarbonates. A plastics lens material known commercially as CR39 is the most commonly used material for manufacture of lenses and the heliochromic chromenes described herein and can be incorporated into preformed lenses manufactured from this material by imbibition.

Imbibition can be conducted by immersion in a solution of the heliochromic compound. Fluorinated solvents are preferred since they are inert and have a high boiling point. Immersion in a saturated solution of the heliochromic compound in the refluxing solvent is a convenient procedure. Preferred solvents are the FC range of perfluorinated hydrocarbon solvents available from the 3M Company and the similar PP range of fluorinated solvents available from ISC Chemicals Limited.

Lenses having the desired colouration to brown in U.V. light can be produced by treating the preformed lenses either simultaneously or sequentially with a yellow colouring heliochromic compound and with a blue colouring compound. For example, the compound of Example 6 of our copending U.K. application No. 8611837 was dissolved in a perfluorinated solvent available from the 3M company under the trade name FC40 (boiling point 165° C.) to form a saturated solution and a lens made from CR39 plastic was immersed in the refluxing solution for 30 minutes. The lens was then immersed in a solution in the same solvent of the compound described in Example 1 of this specification under similar conditions for 30 minutes. The resulting lens coloured to brown when subjected to a 1000 watt lamp simulating solar radiation.

As an alternative to immersion in a solution of the heliochromic compounds, imbibition may be effected by exposing the lens to the vapour of the heliochromic compound. This may be achieved, e.g. by heating the heliochromic compound in a vacuum chamber in the presence of the lens to be treated. Heating at a temperature of about 160° C. for about 1 hour under a vacuum of less than about 0.25 m bar, resulted in lenses which coloured on exposure to U.V. light. The imbibition effect is improved by pretreating the plastic lenses by immersion in refluxing tetrahydrofuran for one hour.

The accompanying absorption spectra (FIGS. 1 to 8) illustrate typical photochromic properties of the blue-colouring heliochromic compounds of this invention. In all cases the lower curve represents the compound in question in its colourless state and the upper curve after exposure to a flash gun. As compared with the spiro-adamantane compounds described in our co-pending patent application No. 86 11837, the compounds of this invention absorb strongly in the 500 to 600 nm region. Referring, for example, to FIG. 1, the lower curve represents the compound in its colourless state and the upper curve after irradiation with a lamp simultating sunlight. FIG. 2 shows the behaviour of the bis-chromene of Example 8. Again, the lower curve represents the compound in its uncoloured state and the upper curve the coloured state. An important advantage stems from the fact that the uncoloured state of this compound absorbs more strongly than the coloured state in the U.V. region. As a consequence, there is a reduced internal filter effect and a larger conversion of the material to the coloured state on irradiation.

Although imbibition from fluorocarbon solvent solutions is the currently preferred method of incorporating the heliochromic compounds into plastics materials, such as CR 39, it is also possible to imbibe the compounds from a melt.

In order to test contact imbibition from the melt as a possible technique a sample of the compound of Example 4 was melted onto a sheet of CR 39 plastic and a second sheet of CR 39 added to form a sandwich. The sample was held at 160° C. for 40 minutes, then cooled and washed with chloroform. The UV/visible spectrum of the imbibed CR 39 shows a Cod of $25.7 \times 10^{-5}$Mcm for imbibition on one side. This compares with a Cod of $19.4 \times 10^{-5}$Mcm achieved when the same compound was imbibed into a sheet of CR 39 from solution in the fluorocarbon solvent 'FC40' marketed by 3M Corporation.

Cod refers to the optical density of the imbibed material in the coloured form.

When incorporating heliochromic compounds into plastics materials either by imbibition or from a melt, it is important to exclude oxygen in order to avoid degradation of the heliochromic compound.

Another method of incorporating the heliochromic compounds into plastics substrates involves including the compound in the plastics material from which the lens is moulded. This technique is described in U.S. Pat. No. 4,576,766.

Although the invention has been described with particular reference to the use of heliochromic compounds for manufacture of photoreactive lenses, it will be appreciated that the compounds also have other uses deriving from their photochromic properties. The compounds can, for example, be used to make variable density filters generally.

We claim:

1. An opthalmic or plano-lens which darkens in sunlight and reverts to a pale or colourless condition in white light at normal ambient temperatures, wherein the lens has incorporated therein or coated thereon at least two heliochromic compounds, one of said compounds comprising an adamantane spiro-benzopyran or spironaphthopyran in which an adamantane group is present in the 2-spiro-position of the benzopyran or naphthopyran ring and a second compound comprising a benzo or naphthopyran having a nitrogen-containing substituent in the 2-position of the pyran ring.

2. A lens according to claim 1 in which one of said heliochromic compounds is an adamantane-spironaphthopyran and a second heliochromic compound has the general formula:

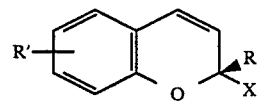

(I)

in which
R represents an alkyl group or an aryl group which may contain a nitrogen containing substituent and R' represents one or more substituents selected from hydrogen, alkyl, halogen, aryl, hydroxy, alkoxy, alkyl- or dialkylamino, or a heterocyclic group and wherein the ring containing the substituent group R' may be benzannelated and
X represents an aryl group having a nitrogen-containing substituent.

3. A lens according to claim 2 in which the group X is a phenyl group having an amino or substituted amino substituent or a nitrogen-containing heterocyclic substituent is in the ortho and/or para-position.

4. A lens according to claim 2 or 3 in which the group R is a phenyl group having an amino or substituted amino substituent or a nitrogen-containing heterocyclic in the ortho and/or para position.

5. A lens according to claim 2 in which the second heliochromic compound has the following general formula:

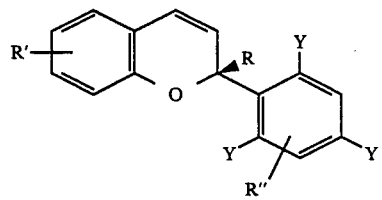

(IA)

in which R has the same significance as in claim 2, each Y represents hydrogen, amino, alkyl- or dialkyl-amino, or a nitrogen-containing heterocyclic group (with the proviso that at least one Y is a nitrogen containing substituent and R' represent one or more substituents independently selected from hydrogen, alkyl, halogen, alkoxy, aryl, amino or substituted amino, or a heterocyclic group or the ring containing the substituent R' is benzannelated and R" represents hydrogen, alkyl, halogen, alkoxy or aryl.

6. A lens according to claim 5 in which the second heliochromic compound has the general formula:

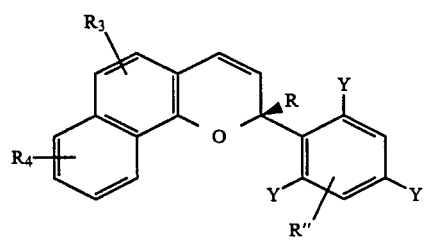

(II)

in which $R_3$ and $R_4$ independently represent one or more substituents selected from hydrogen, lower alkyl, aryl, lower alkoxy, hydroxy, halogen, alkyl- or dialkyl-amino, or a heterocyclic group.

7. A lens according to claim 6 in which $R_3$ represents an alkoxy phenyl group.

8. A lens according to claim 6 or claim 7 in which Y is an amino or substituted amino, morpholino, piperidino, pyridino or pyrrolidino group.

9. A lens according to claim 6 or claim 7, in which the $R_3$ substituent is a lower alkoxy, lower alkoxyphenyl or halogen group, and is present in the 6-position.

10. A lens according to claim 1 in which the second heliochromic compound has the general formula (III):

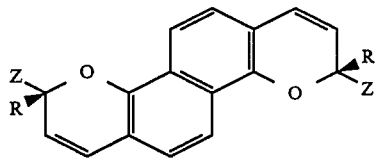

(III)

in which R is an alkyl group or an aryl group and Z represents an aryl group, alkyl or hydrogen.

11. A lens according to claim 10 in which each Z independently represent phenyl or a phenyl group substituted with a primary, secondary or tertiary amino group or with a heterocyclic nitrogen-containing group and R is an alkyl group.

12. A lens according to claim 8, in which the $R_3$ substituent is a lower alkoxy, lower alkoxyphenyl or halogen group, and is present in the 6-position.

* * * * *